United States Patent

Augros

Patent Number: 5,105,827
Date of Patent: Apr. 21, 1992

[54] ELASTIC SPONGE PAD SUCH AS VAGINAL PAD

[76] Inventor: Jacques Augros, Avenue de la Croix-Baillet, 95400 Villiers Le Bel, France

[21] Appl. No.: 436,926

[22] Filed: Nov. 13, 1989

Related U.S. Application Data

[63] Continuation of Ser. No. 181,420, Apr. 14, 1988, abandoned.

[30] Foreign Application Priority Data

Apr. 29, 1987 [FR] France ............................... 87 06124

[51] Int. Cl.⁵ ............................................... A61F 6/06
[52] U.S. Cl. ...................................... 128/832; 128/919; 604/11; 604/55; 604/286; 604/369
[58] Field of Search ............... 604/285, 286, 369, 904, 604/11, 55, 57; 128/830, 832, 834, 894, 887, 919; 2/20, 21, 267; D32/35, 40, 42, 43; 132/317

[56] References Cited

U.S. PATENT DOCUMENTS

| | | | |
|---|---|---|---|
| 70,616 | 11/1867 | Rhees | 128/834 |
| D. 184,234 | 1/1959 | Maccio | D32/43 |
| 1,480,680 | 1/1924 | Glover | 604/11 X |
| 1,634,555 | 7/1927 | Peloubet | 128/834 X |
| 2,097,033 | 10/1937 | McVittie | 604/286 |
| 2,110,962 | 3/1938 | Munro | 604/11 |
| 2,141,026 | 12/1938 | Valle | 604/285 X |
| 2,319,143 | 4/1943 | Levy et al. | 128/894 X |
| 2,389,237 | 11/1945 | Petrullo | 2/21 X |
| 2,539,115 | 1/1951 | Brachman | 128/894 |
| 2,786,446 | 3/1957 | Rudnick | 128/894 |
| 2,827,050 | 3/1958 | Fisher | 128/894 |
| 2,923,292 | 2/1960 | Dorr | 128/894 |
| 3,029,813 | 4/1962 | Hannington | 128/894 |
| 3,036,571 | 5/1962 | Scholl | 128/894 |
| 3,128,762 | 4/1964 | Young | 128/844 X |
| 3,332,429 | 7/1967 | Bates | 132/317 |
| 3,683,904 | 8/1972 | Forster | 128/834 |
| 3,972,325 | 8/1976 | Bluestone | 128/132 R |
| 4,274,410 | 6/1981 | Chuapil | 604/11 X |
| 4,286,593 | 9/1981 | Place et al. | 604/285 |
| 4,300,544 | 11/1981 | Rudel | 128/832 |
| 4,326,510 | 4/1982 | Buckles | 128/832 |
| 4,564,362 | 1/1986 | Burnhill | 604/369 |
| 4,629,449 | 12/1986 | Wong | 604/285 |
| 4,858,624 | 8/1989 | Shihats | 128/834 |
| 4,883,071 | 11/1989 | Pickhard et al. | 128/837 |
| 4,922,928 | 5/1990 | Burnhill | 128/832 |
| 4,959,216 | 9/1990 | Daunter | 424/430 |
| 4,961,436 | 10/1990 | Koch | 128/837 |
| 5,000,749 | 3/1991 | LaVeen et al. | 624/904 |

FOREIGN PATENT DOCUMENTS

| | | | |
|---|---|---|---|
| 24024 | 7/1936 | Australia | 604/286 |
| 84755 | 8/1983 | European Pat. Off. | |
| 290307 | 11/1988 | European Pat. Off. | 604/904 |
| 822877 | 7/1949 | Fed. Rep. of Germany | |
| 828141 | 7/1949 | Fed. Rep. of Germany | |
| 7900014 | 1/1979 | World Int. Prop. O. | 604/11 |

Primary Examiner—C. Fred Rosenbaum
Assistant Examiner—Mark O. Polutta
Attorney, Agent, or Firm—Marshall & Melhorn

[57] ABSTRACT

This pad, such as a vaginal pad, comprises a body in elastic foam and a finger gripping device for inserting or drawing out the pad; the gripping device is a recess formed in the pad body.

12 Claims, 2 Drawing Sheets

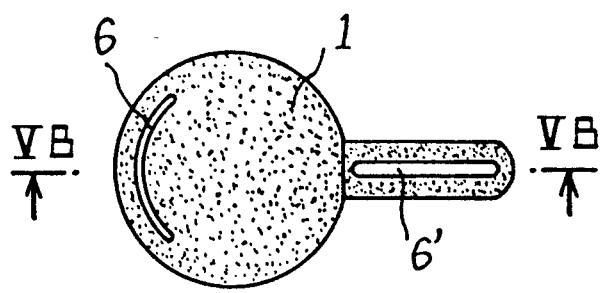
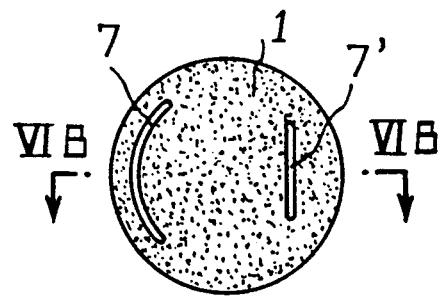
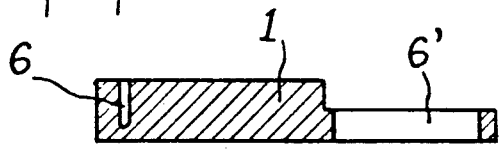
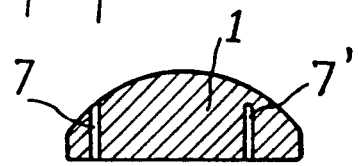
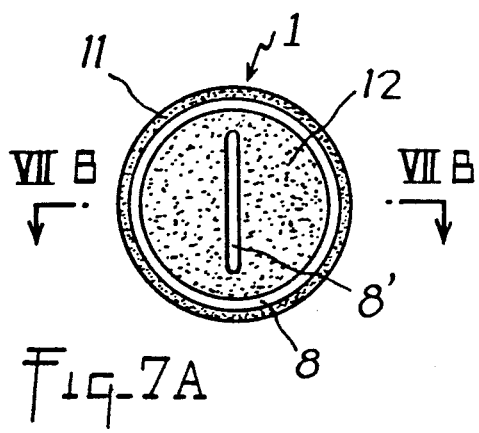
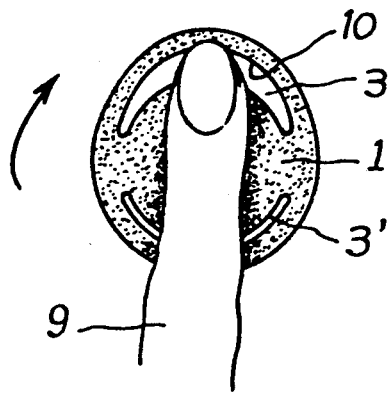
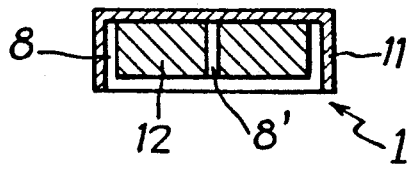
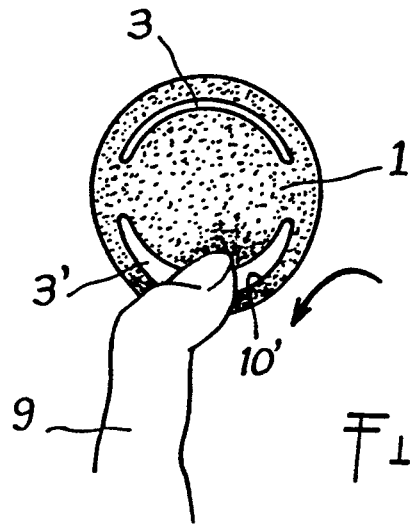

ELASTIC SPONGE PAD SUCH AS VAGINAL PAD

This application is a continuation of application Ser. No. 07/181,420, filed Apr. 14, 1988, now abandoned.

FIELD OF THE INVENTION

The invention relates to a pad constituted of a body in elastic sponge, foam, or similar material.

BACKGROUND OF THE INVENTION

The use, in particular for contraception purposes, of round or flat vaginal pads in sponge, foam or other elastic absorbing substances, impregnated with products having a spermicidal or medicinal action, has been known for many years.

Although these pads are relatively easy to insert by hand, their extraction after use is often difficult and unpleasant for women when no extraction means are provided. For this reason, some of the known pads are provided with added digital holding means, such as a loop (see EP-A-29708), or a thread (see FR-A-2 463 609 or WO-A-80/00 0008) by which the pad can be gripped and pulled out. But such holding means, which are external to the body of the pad, are a hindrance to any couple, by its very presence and hardness; it can be felt and cause irritations of both parties. This has considerably limited the development of this contraception method.

OBJECT OF THE INVENTION

It is the object of the invention to overcome the aforesaid drawbacks and to propose a pad offering an easy hold and permitting an easy extraction after use.

The object is reached with a pad in which the holding device is produced by a recessed part of the pad body. Said recessed part has at least one edge substantially perpendicular to a surface of the pad body and enables the finger to rest on said edge in order to move the pad, either to insert it or mainly to pull it out.

It must be understood that the invention bears no relation to the cavities or orifices which are sometimes provided in pessaries. On the one hand, such pessaries are generally produced from another material than an impregnable foam (DE-C-828 141 or EP-A-84 755) and the problems arising are therefore different from those of the invention. On the other hand, the object of the orifices is not to constitute gripping means for the fingers; in the known sponge devices, even though recessed parts may be provided for different purposes, they do not exclude the presence of other gripping devices (DE-C-822 877 or U.S. Pat. No. 4,564,362.

The recessed part according to the invention is created by a separation localized in the texture of the product, and obtained by cutting out, machining or molding, at any stage in the production of the pad. Preferably, the recess is formed by cutting with either a hollow punch or a blanking die, advantageously at the same time as the pad itself, from a primitive blank. Said recess is constituted by an elongated through or blind slit. In its most advantageous form, the recess is an extremely narrow slit or a cut, obtained by a simple cutting or stamping in the foam pad.

Advantageously, the recess is off-centered, situated marginally and substantially in parallel to an edge of the body; if it is a through recess it then forms a loop.

It is of course possible to have one or more recesses: in particular, it is advantageous to have two recesses, one for fitting in the pad and another for pulling it out, respectively. These recesses are preferably situated in two opposite zones of the pad so that insertion of the pad by way of the first recess makes it possible to position at the same time the opposite recess in the lower position, this making the pad easier to hold with the index for withdrawal.

The recesses can be rectilinear, or in arc of circle, or they can have different shapes and orientations, depending on the intended purpose, on the configuration and on the volume of the pad.

Said pad is generally round and flat-shaped, but other shapes are also suitable.

Given that said recesses are made in the actual body of the pad, no foreign body can be introduced with the pad. Moreover, these recesses can be produced at very low cost.

An introduction-extraction means can of course be used for fitting in and drawing out the pad, its use and reliability being reinforced by the presence of the recesses according to the invention.

The invention also finds other applications besides contraception and the prevention of sexually transmitted diseases such as AIDS. Indeed, outside the medical field, the invention can relate to pads for industrial cleaning or household use, or for use in cosmetology, or in any other applications where a grip or a hold is required.

BRIEF DESCRIPTION OF THE DRAWINGS

The invention will be more readily understood on reading the following description with references to the accompanying drawings, in which:

FIGS. 5A and 5B illustrate a fifth embodiment in plan view and in cross-section along V—V, FIGS. 6A and 6B illustrate a sixth embodiment in plan view and in cross-section along VI—VI, FIGS. 7A and 7B illustrate a seventh embodiment in plan view and in cross-section along VII—VII, FIGS. 8 and 9 illustrate the method of fitting in and extracting the pad according to the invention.

DETAILED DESCRIPTION OF THE INVENTION

Figure 1A:
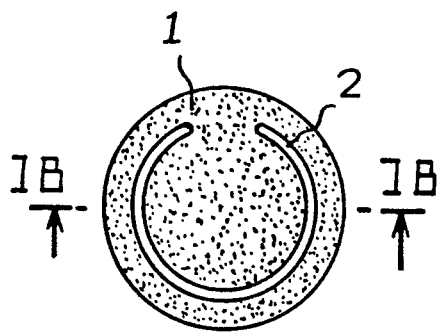
FIGS. 1A and 1B illustrate a first embodiment in plan view and in cross-section along I—I.
Figure 1B:
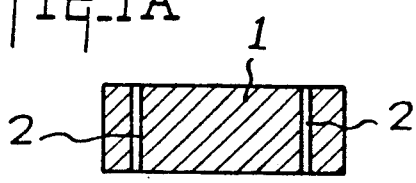
Figure 2A:
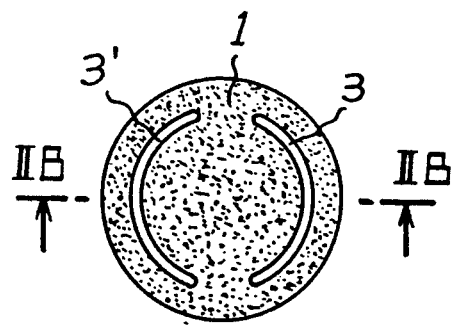
FIGS. 2A and 2B illustrate a second embodiment in plan view and in cross-section along II—II.
Figure 2B:
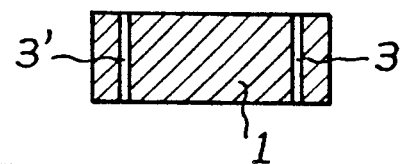
Figure 3A:
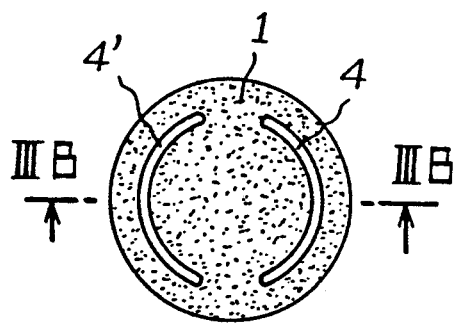
FIGS. 3A and 3B illustrate a third embodiment in plan view and in cross-section along III—III.
Figure 3B:
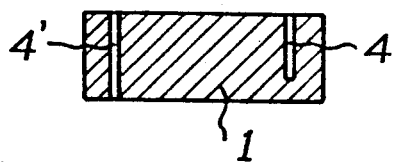
Figure 4A:
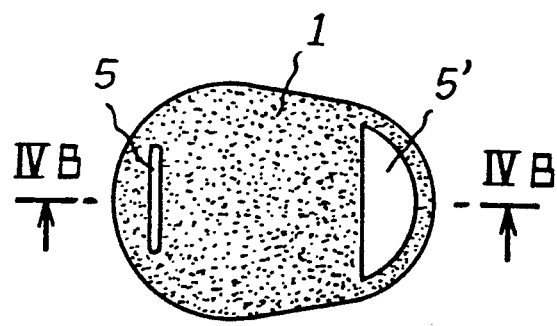
FIGS. 4A and 4B illustrate a fourth embodiment in plan view and in cross section along IV—IV.
Figure 4B:
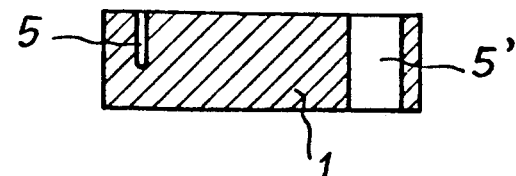

The pad comprises a body 1 in impregnatable elastic sponge produced in an open pore foam. In said body 1 is provided a recess 2 to 8' (FIGS. 1 to 7) in which the finger 9 (FIGS. 8, 9) can be partly introduced in order to grip one of the side walls 10, 10' of recess 3, 3' for inserting (FIG. 8) or extracting (FIG. 9) the pad, and this because of the deformability of the material constituting the body 1.

The recess can be relatively narrow and elongated (as illustrated in all the drawings), hence have a high length/width ratio. In fact the recesses in FIGS. 1, 2 and 3 for example are preferably simple cuts (a width is shown in the figures for clarity's sake) obtained by a single slitting operation made in the pad. Said operation can be simultaneous with the pad general cutting operation.

The pad is of general cylindrical flattened shape. The cylinder can have an annular base (FIGS. 1,2,3,7) or a non-annular base: for example a trapezoidal base which is rounded (FIG. 4) or circular with an appendix (FIG. 5) is also suitable.

One base or the bases of the cylinders can be flat (FIGS. 1,2,3,4) or staggered (FIG. 5) or skew (FIG. 6).

Recesses 2, 3, 3', 4', 5', 6', 7 traverse the whole thickness of the pad, whereas recesses 4, 5, 6, 7', 8, 8', are blind spots.

The advantages of the through recesses is that they separate completely the body of the pad at their level, thereby permitting a greater deformation and a greater stretching of one of the lips of the recess (FIGS. 8,9). When the through recess is made along one edge of the pad, a loop forms which helps to grip the pad (FIGS. 8,9). Contrary to the known devices, the fact of pulling out the pad of the invention by means of a loop, avoids gripping and pushing the pad itself, which causes said pad to reject a fair quantity of the product with which it is impregnated, hence a loss of active product and a discomfort for the user.

The advantage of blind recesses on the contrary is that they are more resistant or that they can have a closed outline. (recess 8, FIG. 7).

It is of course possible to combine on the same pad, through recesses with blind recesses.

When a pad is provided with two recesses, these should advantageously be situated in two opposite parts of the pad (FIG. 2,3,4,5,6,8,9) so that they can be used respectively for inserting (FIG. 8) and for extracting (FIG. 9) the pad by means of finger 9. The recesses are preferably situated on the edge of said opposite parts so that most of the body 1 can be drawn out.

The same effect can also be obtained with only one recess provided in two opposite parts of the pad, preferably marginally (FIG. 1, recess 2) or in the center (FIG. 7, recess 8).

The recesses are created directly in the body of the pad by simple cutting, sawing, machining or any other method.

The pad can, optionally, comprise assembled pieces, such as illustrated in FIGS. 7A, 7B in which the body 1 is formed of a first part 11 in the shape of a bowl with cylindrical edge, at the bottom of which is added a second part 12 shaped as a disc. The recess 8 if formed by the space left between the inner edge of bowl 11 and the outer edge of disc 12. The assembled pieces may have different characteristics of hardness, absorption power, isolation, diffusion, surface condition, etc. They can optionally be impregnated with different or incompatible products, such as products reacting together (foaming products), or products having complementary actions, or being micro-encapsulated.

I claim:

1. A vaginal pad for preventing conception and transmission of sexually transmitted disease, comprising a monolithic body of a singular pliable foamed elastic material adapted to receive an effective amount of a spermicidal agent, said body being uninterrupted at the center thereof, and including marginally positioned digital holding means for holding, inserting the pad into and extracting the pad from the vaginal canal of the user, wherein said digital holding means is in the form of a recess extending through the entire thickness of said body.

2. Pad as claimed in claim 1, wherein the recess is an elongated slit.

3. Pad as claimed in claim 1, wherein the recess forms a loop.

4. A vaginal pad as defined in claim 1, wherein two marginally positioned recesses are provided for respectively inserting and drawing out the pad said recesses being disposed opposite one another.

5. Pad as claimed in claim 1, wherein the body is of substantially cylindrical flattened general shape.

6. Pad as claimed in claim 1, wherein the recess is situated marginally and substantially in parallel to one edge of the body.

7. Pad as claimed in claim 1, wherein the recess has at least one set back edge substantially perpendicular to a contiguous surface of the body of the pad, forming a rest for one finger, for inserting or drawing out the pad.

8. A vaginal pad for preventing conception and transmission of sexually transmitted disease, comprising a monolithic body of a singular pliable foamed elastic material adapted to receive an effective amount of a spermicidal agent, said body being uninterrupted at the center thereof, and including marginally positioned digital holding means for holding, inserting the pad into and extracting the pad from the vaginal canal of the user, wherein said digital holding means is in the form of an elongate slit in said body.

9. A vaginal insert for preventing conception and transmission of sexually transmitted disease comprising, a monolithic body of a singular, pliable, foamed elastic material adapted to receive an effective amount of a spermicidal agent, said body including a flat pad having a generally circular outline and oppositely disposed generally planar surfaces, at least one elongate slit extending through said pad, said slit defining an opening in said pad having opposite walls extending transversely between said planar surfaces, said slit normally remaining closed with said pad in place for use, and said pad being adapted to deflect adjacent said slit in response to digital pressure and expose said walls to digital engagement for inserting the pad into and extracting the pad from the vaginal canal of the user.

10. A vaginal insert as claimed in claim 9, wherein said slit is spaced inwardly from and extends along said circular outline for a distance greater than one-half the circumference of said pad so as to form said walls at diametrically opposite locations around said pad.

11. A vaginal insert as claimed in claim 9, including a pair of said elongate slits, each slit of said pair being spaced inwardly from and extending along said circular outline, and said slits being diametrically opposite one another around said pad whereby said walls at one of said slits accommodates digital engagement for inserting said pad and said walls at the other of said slits accommodates digital engagement for extracting said pad.

12. A vaginal pad as claimed in claims 1, 8 or 9 wherein the recess is obtained by a single cutting operation simultaneous to the pad cutting operation.

* * * * *